Figure 2:
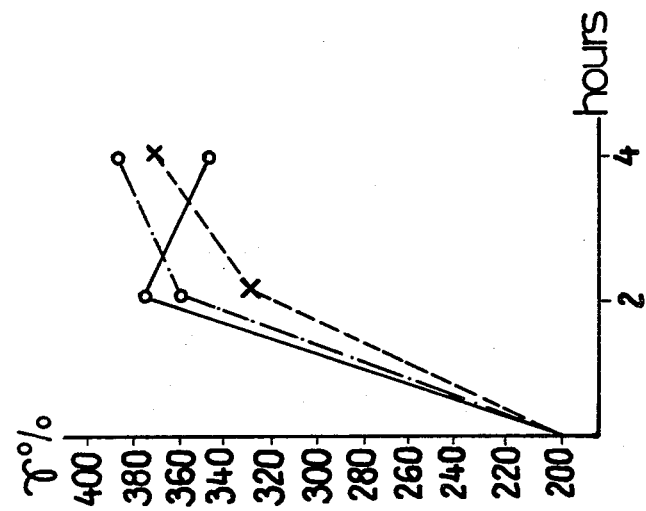

United States Patent [19]

Lakatos et al.

[11] 4,225,592
[45] Sep. 30, 1980

[54] COMPLEXES OF OLIGO- AND POLYGALACTURONIC ACIDS FORMED WITH ESSENTIAL METAL IONS AND PHARMACEUTICAL PREPARATIONS CONTAINING THE SAME

[76] Inventors: Bela Lakatos, 17 Tarcsay V. utca, 1026 Budapest; Julia Meisel nee Agoston, 39-41 Ulaszlo ut, 1113 Budapest; Mihaly Varju, 9 Kuny utca, 1012 Budapest, all of Hungary

[21] Appl. No.: 11,421

[22] Filed: Feb. 12, 1979

Related U.S. Application Data

[60] Division of Ser. No. 901,835, May 1, 1978, abandoned, which is a continuation-in-part of Ser. No. 782,050, Mar. 28, 1977, abandoned.

[30] Foreign Application Priority Data

Mar. 31, 1976 [HU] Hungary .............................. MA 2754

[51] Int. Cl.$^3$ ....................... A61K 31/70; C07H 23/00
[52] U.S. Cl. ..................................... 424/180; 426/658; 426/659; 426/660; 536/121
[58] Field of Search ......................... 424/180; 536/121

[56] References Cited

U.S. PATENT DOCUMENTS

| | | | |
|---|---|---|---|
| 2,518,135 | 8/1950 | Gauer | 536/121 |
| 3,074,927 | 1/1963 | Saltman et al. | 536/121 |
| 3,563,978 | 2/1971 | Ochs | 536/121 |

OTHER PUBLICATIONS

Charley et al., "Biochimica et Biophysica Acta", vol. 69, 1963, pp. 313–321.
Waldron–Edward, "Nature", vol. 205, Mar. 1965, pp. 1117–1118.
Kostial et al., "Reprint from Environmental Research", vol. 4, No. 4, Oct. 1971.

*Primary Examiner*—Johnnie R. Brown
*Attorney, Agent, or Firm*—Young & Thompson

[57] ABSTRACT

Novel complexes of oligo- and polygalacturonic acids formed with essential metal ions and having the general formula (I),

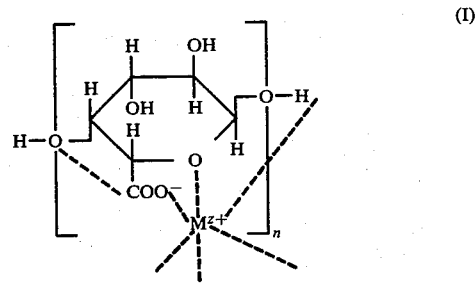

wherein
n is an integer from about 10 to about 145
M represents at least two metal cations selected from the group consisting of iron(II), copper(I), copper(II), magnesium(II), potassium(I), cobalt(II), manganese(II), zinc(II), chromium(III), molybdenum(V), vanadium(IV) and nickel(II) with the proviso that one of the ions must represent potassium(I) or magnesium(II), and
z is an integer corresponding to the charge or the valence number of the metal atom
are useful in foodstuffs and pharmaceutical preparations for administering essential elements to humans.

1 Claim, 2 Drawing Figures

COMPLEXES OF OLIGO- AND POLYGALACTURONIC ACIDS FORMED WITH ESSENTIAL METAL IONS AND PHARMACEUTICAL PREPARATIONS CONTAINING THE SAME

CROSS-REFERENCE

This application is a divisional application of our copending application Ser. No. 901,835, which was filed May 1, 1978, now abandoned as a continuation-in-part application of our copending application Ser. No. 782,050 filed on Mar. 28, 1977 and now abandoned.

The invention relates to a method for treating a deficiency of essential metal ions in humans, by administering to humans suffering in such deficiency complexes of oligo- and polygalacturonic acids formed with essential metal ions.

The novel compounds useful in the practice of methods according to the invention have the general formula (I),

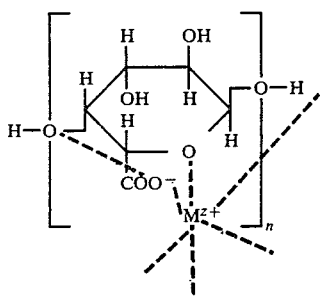

wherein
n is an integer from about 10 to about 145,
M represents at least two metal cations selected from the group consisting of iron(II), copper(I), copper(II), magnesium(II), potassium(I), cobalt(II), manganese(II), zinc(II), chromium(III), molybdenum(V), vanadium(IV) and nickel(II) with the proviso that one of the ions must represent potassium(I) or magnesium(II), and
z is an integer corresponding to the charge or the valance number of the metal atom.

BACKGROUND OF THE INVENTION

As is known, the "essential elements", i.e. calcium, magnesium, sodium and potassium, furthermore zinc, manganese, copper, cobalt, chromium, iron, molybdenum, vanadium and nickel are indispensable for the normal function of living organisms. The essential elements are the constituents or activators of numerous enzyme systems, they are in close correlation with the level of certain vitamins in the organism and with the function of the hormone system. The deficiency of essential elements greatly suppresses the biosynthesis of proteins, enzymes, hormones and other biologically active substances required to control the normal functions of the living organism as a whole.

It is also known that the essential element content of foodstuffs of animal and vegetable origin shows a steady decreasing tendency. This can be attributed mainly to the fact that owing to the growing intensity of plant cultivation the concentration of macro and micro elements of the soil absorbable by plants decreases gradually, and the fertilizers containing nitrogen, phosphorous, potassium and optionally calcium (as gypsum or lime), now generally applied in agriculture, are unable to supplement the essential elements (except potassium and calcium) removed from the soil. The subsequent processing purification and refinement of foodstuffs may further decrease the initially low amount of essential elements, frequently below the limit of analytical detection. Therefore, the essential elements which are unavailable from foodstuffs must be introduced into the organism from other sources.

So far, the essential elements were administered to the living organisms mainly in ionic state (as inorganic salts or sometimes as simple organic salts). These compounds were administered orally, particularly by mixing the metal salts into foodstuffs (J. Am. Dietetic Assoc. 59, 27 (1971)). However, the application of simple metal salts does not ensure good absorption and biological utilization of the essential elements, since metal salts form hardly soluble compounds (oxides, hydroxides, sulfides, phytates, etc.) in the living organism by interaction with the chymus or with some components of food or their digestion products. The metals are removed from the organism in the form of hardly soluble compounds without any appreciable biological utilization. A further disadvantage is due to the unpleasant taste of simple metal salts, which greatly restricts the amount of metal that can be mixed into foodstuffs. Moreover, the metal salts may catalyze the decomposition of easily oxidizable vitamins present in the foodstuffs.

Slightly better utilization can be ensured by administration of the essential elements to the living organism as organic chelates (e.g. complexes formed with EDTA, aspartic acid, glutamic acid, citric acid, etc.). The applicability of these compounds is, however, rather limited, since their great thermodynamical stability reduces the efficiency of metal utilization and these chelates may even remove important other trace elements from the organism. Thus e.g. the introduction of citrates in larger amounts may lead to anaemia or may aggravate the already existing anaemic state, since citric acid forms a stable complex with iron thereby removing it from the organism, and citrates also hinder the absorption of copper, an element of crucial importance in the treatment of anaemia. The overdosage of citrates or aspartates may also lead to the development of nephroliths.

Previous investigations have shown that the problem concerning the absorption and utilization of essential elements can be reduced considerably by introducing metals into the living organism in the form of appropriate biopolymer-metal chelate complexes.

The Hungarian patent specification No. 158,252 describes the preparation and biological effects of metal complexes formed with humic acid. Metal humates are readily absorbed in the living organism, but their use is strongly limited by the fact that humic acids are chemically undefined substances with widely varying composition and metal binding ability, and thus metal complexes of uniform and reproducible quality cannot be prepared from humic acids. Consequently, metal humates do not provide well defined and predictable biological effects and may also exert unpredictable and undesired side effects in the living organisms.

Of the biopolymer-iron systems specially suitable for the administration of iron, the mixed complexes chrondroitin sulfate-iron(II)-iron(III), alginic acid iron(II)-iron(III), pectin-iron(II)-iron(III) and degraded casein-iron(II)-iron(III) have been reported in the literature (published Japanese patent application No. 69 02.802; Yakugaku Zasahi 90, 120–126 (1970); Yakugaku Zasshi 90, 1480–1487 (1970); Japanese patent specification No. 13,090 (Chem. Abstr. 60, 5287f); Belgian patent specification Nos. 619,267 and 652,508). The alginic acid-iron-(II)-iron(III), pectin-iron(II)-iron(III) and degraded casein-iron(II)-iron(III) systems are, like metal humates, chemically ill-defined compositions, which therefore do not ensure predictable and reproducible biological responses. Although the complex chondroitin sulfate-iron(II)-iron(III) is well defined both chemically and biologically, it has the disadvantage that the natural sources of chondroitin sulfate, required as starting substance, are very limited, and the isolation and purification of this compound is a complicated, tedious procedure.

U.S. Pat. No. 3,074,927 discloses metal complexes of reducing sugars such as iron(III) fructose and U.S. Pat. No. 2,518,135 describes metal complexes of 2-substituted glycopiranose derivatives. Although these complexes may be also used for introducing metal ions into a living organism, they are absorbed in a much smaller amount than the complexes of the invention.

Journal of Polymer Science, 10,A-I 287 to 293 (1972) discloses complexes of polygalacturonic acids formed with copper(II), cadmium(II), zinc(II) and nickel(II) ions, respectively. In these complexes the polymerization grade of the polygalacturonic acids, i.e. n is at least 150, preferably 150 to 400, according to the producer of these polygalacturonic acids, i.e. the firm ICN Pharmaceuticals, Inc., Cleveland, Ohio. However, due to the high molecular weight of the polygalacturonic acids employed in these complexes the latter are absorbed by the living organism in a much smaller amount than the complexes of the present invention. Accordingly, the complexes of the cited literature reference are not applicable for introducing essential elements into a living organism. In sharp contrast, the polygalacturonic acids of these complexes are used for removing from a living organism toxic elements such as lead and radioactive strontium. U.S. Pat. No. 3,563,978 discloses metal complexes formed with carboxymethyl cellulose, naturally occurring alginates, naturally occurring carrageenins and mixtures thereof. These complexes may be used for removing bile acids from a living organism and thus for preventing reabsorption of these acids by the small intestine. Accordingly, these complexes are not absorbed by the cells of a living organism.

It is known from French Pat. No. 860 M that hypokalaemia may be treated by administering a potassium salt of polygalacturonic acid. However, this patent fails to teach why such a salt is preferable for treating said deficiency in view of the fact that several simple salts of potassium such as the corresponding chloride or citrate are well absorbed by the living organism and are therefore usable for treating hypokalaemia.

Our aim is to produce chemically and biologically well defined biopolymer-metal complexes which ensure predictable and reproducible biological responses, release the complexed essential metals quickly and quantitatively to the oligo- and polypeptides and mucopolysaccharides of the living organism when introduced, and which can be prepared by simple methods from easily available starting substances. We have found that the compounds of the general formula (I) fully meet the above requirements. Further, we have found that the potassium or magnesium ions contained in the complexes of the invention are able to replace some of the calcium ions closing the membranes of the cells and thus make it possible for the other metal ions contained in the very same complex to come through the membrane and be absorbed by the cell.

Thus the invention relates to novel complexes of oligo- and polygalacturonic acids formed with essential metal ions and having the general formula (I), wherein n, M and z are as defined above.

The complexes of the invention may be prepared by methods known per se. Preferably one proceeds by reacting an oligo- or polygalacturonic acid of the general formula (II),

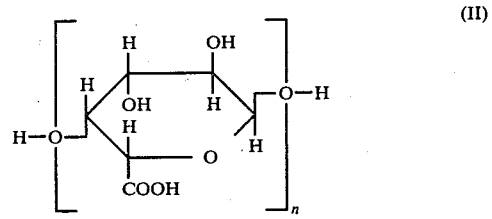

wherein n is as defined above, with at least two salts containing $M^{z+}$ ions, wherein M and z are as defined above, or with at least two complexes of metals M which have lower stability constants than the corresponding oligo- or polygalacturonic acid-metal complex (such as acetate complexes). However, potassium may also be used in the form of its hydroxide. According to our experiments this form is the most preferable. The reaction is performed in aqueous and/or polar organic media or in solid phase.

The term "metal ion" used in the specification and claims also includes the positive ions composed of metal and oxygen atoms, such as the $[Mo(O)]^{3+}$ ion.

We have found that the biological effects of complexes in which several types of essential metal ions are complexed by one molecule are more favorable than those of the physical mixtures of oligo- and polygalacturonic acid complexes each containing only one type of essential metal ion. By the proper selection of the ratios of the metal salt or metal complex reactants, the ratios of the metal ion types in these "polymetal complexes" or "coprecipitates" can be varied over a wide range. The coprecipitates can be applied particularly well e.g. in the treatment of anaemia, since in this instance the complete set of essential elements required for the treatment (iron, copper, cobalt, manganese, zinc, molybdenum) can be introduced into the organism with a single composition. The coprecipitates can also be used to great advantage e.g. for the treatment of diabetes, for the prophylaxis of cardiac infarction, atherosclerosis and nephrolithiasis, for the promotion of wound healing and also in geriatrics.

As mentioned above, the novel compounds of the general formula (I) can be converted into pharmaceutical compositions for oral administration, or can be mixed into foodstuffs.

For the preparation of pharmaceutical compositions, the essential metal ion complexes of decagalacturonic acid (n=10) have proved to be particularly advantageous. Pharmaceutical compositions for oral administration, e.g. tablets, capsules, pills, suspensions, etc., can be prepared by conventional procedures. If desired, the active agents of the general formula (I) can be admixed with other biologically active substances (such as vitamins) and/or conventional pharmaceutical vehicles, such as diluents, carriers, disintegration aids, adjuvants, etc. The pharmaceutical compositions may also contain more than one metal biopolymer of the general formula (I). Owing to their favorable physical characteristics, the compounds of the general formula (I) can also be tableted directly, without any auxiliary agent.

As mentioned above, the compounds of the general formula (I) can also be prepared by solid-phase reactions. Such a reaction occurs when a homogeneous mixture of the starting substances, i.e. of an oligo- or polygalacturonic acid of the general formula (II) and at least two metal salts or complexes containing $M^{z+}$ ions, is tableted. Under the great pressure applied in tableting, the reaction starts in solid phase and the required metal complexes are formed in the stomach.

To increase the essential metal content of foodstuffs, the essential metal ion complexes of a polygalacturonic acid with n being equal to about 140 are preferable. These compounds can be added to foodstuffs (such as chocolates, sausages, dairy products, breads, cakes, fruit products, syrups, etc.) according to known procedures.

It should be mentioned that the terms "pharmaceutical composition" and "foodstuffs" are used in the broadest sense; they also pertain e.g. to infant formulas, dietetic products, etc.

It is also noteworthy that metal salts and/or metal complexes which contain the essential metals in higher oxidation states than specified above can also be applied for the preparation of the compounds having the general formula (I). In such cases the resulting oxidized intermediates are reduced by generally used methods to obtain the required end-products.

The following part of the specification concerns biological tests performed with compounds of the general formula (I) and the results obtained.

ABSORPTION TEST ON RATS

Male albino rats from the OETI stock breed with body weight of 200 to 300 g. were used as test animals. Each test was performed on a group of 10 animals.

Figure 1:
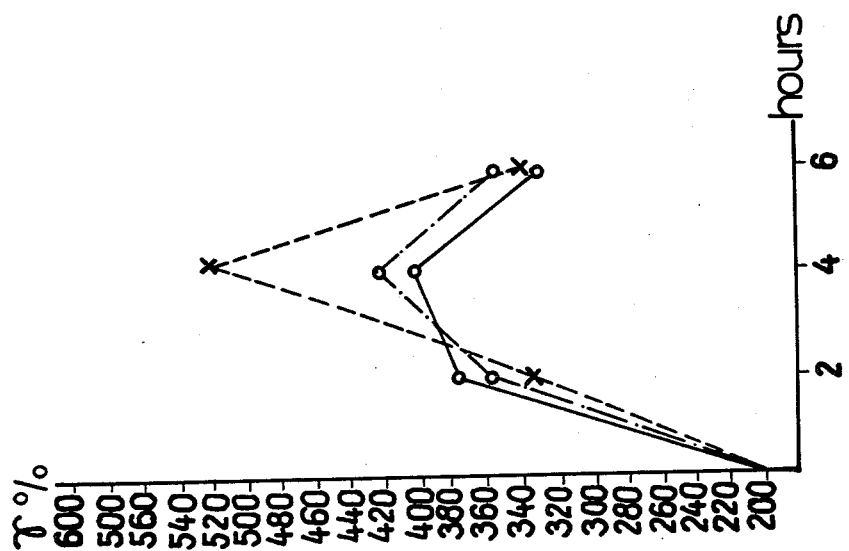

In the first series of tests the animals received an iron - copper - cobalt - potassium complex of polygalacturonic acid (formula (I), M=Fe, Cu, Co, K; n=about 140, z=2) in a single oral dose corresponding to 0.5 mg. of iron/100 g. body weight, 0.05 mg. of copper/100 g. body weight, 0.3 mg. of potassium/100 g. body weight and 0.005 mg. of cobalt/100 g. body weight. The group of reference animals received the same dosages of iron, copper, potassium and cobalt in the form of metal humate or inorganic sulfate mixtures. 2, 4 and 6 hours after administration blood samples were taken from the animals and the iron content of the serum was determined. The results are shown in FIGS. 1 and 2. FIG. 1 shows the results obtained with iron deficient animals, whereas FIG. 2 shows those obtained with normal rats.

As appears from FIG. 1, in iron deficient animals the iron content of the blood serum taken 4 hours after administration of the novel metal biopolymers is significantly higher than that of the animals treated with metal humates or inorganic metal salts. The difference in serum iron content was lower for animals treated with metal humate and inorganic metal sulfates, respectively, than for animals treated with the novel metal biopolymer and metal humate, respectively.

SUBACUTE TOXICITY TESTS ON RATS

Albino male and female rats from OETI stock breed with body weight of 200 to 300 g. were treated for 3 months with the compositions described in the previous test, the daily iron(II), copper(II, potassium and cobalt-(II) consumption was, however, about five times that of the absorption experiments. Thereafter the animals were sacrificed, the spleens were removed, and their iron content was determined. The results are summarized in Table 1.

Table 1

| Composition | No. of animals | Sex | Iron content μg./1 g. of spleen |
| --- | --- | --- | --- |
| Formula (I) compound | 20 | male | 1600 ± 200 |
| | 20 | female | 2000 ± 500 |
| Inorganic metal salts | 20 | male | 600± 100 |
| | 20 | female | 750 ± 100 |
| Metal humate | 20 | male | 1400 ± 200 |
| | 20 | female | 2020 ± 500 |

Macroscopical histological examinations have shown no sign of pathological symptoms, e.g. haemosyderosis. The iron content of the spleen, which is not only the store but also the main erytrocyte-developing organ in rodents, has increased remarkably after treatment with compounds of the general formula (I).

CLINICAL TESTS

(A) Treatment of anaemia

The tests were performed on anaemic female volunteers. A decagalacturonic acid coprecipitate (formula (I), M - Fe, K, Cu, Co, Zn, Mn, Cr, Mo; z=2, 3, 5; n - about 10) corresponding to 15 mg. of iron, 5 mg. of copper, 1 mg. of cobalt, 12 mg. of zinc, 7 mg. of manganese, 0.2 mg. of chromium, 0.1 mg. of molybdenum and 19 mg. of potassium, furthermore 0.5 g. of vitamin C and 15 mg. of vitamin E pro 70 kg. body weight were administered to the patients in single daily dosages after the main meal. The results observed are summarized in Table 2.

Table 2

| Name | Mrs. G. H.~F. | | Mrs. E. B. | | Mrs. I. K. | | Mrs. G. K. | |
| --- | --- | --- | --- | --- | --- | --- | --- | --- |
| Date of examination | 28.3. 1974 | 6.6. 1974 | 11.2. 1969 | 17.1. 1975 | 10.5. 1974 | 2.3. 1975 | 22.5. 1974 | 9.9. 1974 |
| Red blood count (million) | 3.2 | 4.1 | — | — | — | 4.15 | 3.8 | 4.1 |
| Haemoglobin (g. %) | 9.2 | 11.8 | 8.0 | 12.5 | 7.8 | 13.4 | 10.2 | 12.1 |
| White blood cell count | 6000 | 4600 | 6800 | 4800 | — | 6800 | — | 5800 |
| Iron content of the serum (μg. %) | 40 | 120 | 64 | 110 | 79 | 238 | 52 | 96 |
| Saturation iron capacity (μg. %) | 400 | 300 | 300 | 280 | — | 438 | 422 | 232 |
| Saturation index | 10 | 40 | 21 | 39 | — | 54 | 12 | 41 |

Table 2-continued

| Name | Mrs. G. H.–F. | Mrs. E. B. | Mrs. I. K. | Mrs. G. K. |
|---|---|---|---|---|
| (μg. %) | | | | |

The data of Table 2 show that the blood picture of the patients has improved significantly upon the treatment.

(B) Treatment of diabetes

The tests were performed on volunteers. A decagalacturonic acid coprecipitate (formula (I), n—about 10, M=Mn, K, Cu, Mg, Zn, Cr; z=2, 3) corresponding to 15 mg. of magnesium, 2 mg. of chromium, 12 mg. of manganese, 5 mg. of copper, 15 mg. of zinc and 25 mg. of potassium pro 70 kg. body weight was administered daily to the patients for 3 months. The fasting blood sugar level of the patients was measured before and after treatment. The results are given in Table 3.

Table 3

| | Blood sugar level, mg./100 ml. | |
|---|---|---|
| Name | Before treatment | After treatment |
| S.N. | 240 | 92 |
| Gy.N. | 280 | 110 |
| L.K. | 180 | 70 |
| Mrs. I.K. | 270 | 80 |
| Z.A. | 220 | 60 |
| I.Sz. | 350 | 120 |

The data of Table 3 show that the blood sugar level of the patients has become normal upon treatment.

(C) Treatment of magnesium deficiency

The tests were performed on volunteers. Magnesium-potassium-decagalacturonate (formula (I), n=about 10, M=Mg and K, z=2 and 1) corresponding to 40 mg. of magnesium and 20 mg. of potassium pro 70 kg. body weight was administered daily to the patients for 3 weeks. The magnesium content of the blood serum was determined before and after treatment. The results are given in Table 4.

Table 4

| | Magnesium content of the serum, mg. % | |
|---|---|---|
| Name | Before treatment | After treatment |
| Mrs. Gy.N. | 1.3 | 2.7 |
| Mrs. Gy.T. | 2.2 | 4.1 |
| Gy.N. | 1.6 | 3.2 |
| Mrs. L.F. | 1.7 | 4.0 |
| Mrs. I.L. | 0.86 | 3.9 |
| P.N. | 1.99 | 4.2 |
| M.T. | 1.8 | 3.0 |
| B.Sz. | 1.7 | 2.9 |
| Mrs. R.F. | 2.7 | 3.7 |

The data of Table 4 show that the magnesium content of the serum has increased considerably after the treatment.

(D) Treatment of cardiovascular disorders and atherosclerosis

It is known that cardiovascular disorders and atherosclerosis are treated mainly with organic complexes of magnesium such as citrate and aspartate [see e.g. F. Fischer et al: —Ger. Off. 1,809,119 (1968)]. The nine volunteers of the tests performed with a complex of the invention defined below were treated with magnesium-potassium aspartate (sold under the trademark Tromcardin by the Hungarian firm Richter Gedeon and Co.) for about one year in a daily dose of 217.2 mg. of potassium and 70.8 mg. of magnesium pro 70 kg. of body weight. However, despite this treatment the patients were not free of disorders. The volunteers were thereafter treated with the complex described in treatment (C) above in the same doses for the same period. After this treatment the patients were symptomless.

(E) Treatment of nephrolithiasis

It is known that the renal calculi mainly (about 60 percent) consist of calcium oxalate and the probability of forming such calculi may be decreased by orally administering magnesium-containing complexes which are well absorbed by the organism (this is due to the fact that the solubility of magnesium oxalate is much greater than that of calcium oxalate). In the prophylaxis of renal calculi another possibility resides in administering in the form of well-absorbable complexes trace elements (e.g. manganese, copper and iron) which activate the enzymes capable of transforming oxalic acid or inhibit the enzymes capable of forming oxalic acid in the glyoxalate cycle [L. Hagler and R. H. Herman: "Oxalate metabolism", I–V., Am. J. Clin. Nutr., 26, 758 to 765, 882 to 889, 1006 to 1010, 1073 to 1079 and 1242 to 1250 (1973)]. By treating four patients suffering from nephrolithiasis (as determined by X-ray) with a daily oral dose of 100 mg. of magnesium, 18 mg. of iron(II), 20 mg. of manganese, 5 mg. of copper(II) and 130 mg. of potassium, and also 50 mg. of $B_6$-vitamin pro 70 kg. body weight (the metals were, of course, added in the form of a complex formed with a polygalacturonic acid having n=about 140) for one year (during this year the patients were prohibited from consuming milk or milk products in order to reduce the amount of the calcium consumed and were prohibited, of course, from consuming foods containing oxalic acid) it was possible to determine by using X-ray test methods that the patients were free of novel calculi or renal sand and the calculi existing previously were not increased.

(F) Wound healing

It is known that for treating burn injuries and ulcers such as leg ulcers, gastric ulcers and bedsores zinc sulfate is administered orally to the patients [see W. J. Pories and W. H. Strain "Zinc and wound healing" in the book "Zinc Metabolism" (the book is edited by A. S. Prased), Editor C. C. Thomas, Springfield, Ill., 1966, 378–393]; and [E. J. Underwood: "Trace elements in human and animal nutrition", Academic Press, N.Y., 1977, 218].

The following comparative test was carried out: Leg ulcers slow in healing were treated, instead of an oral dose of 600 mg. of zinc sulfate, with a complex of the invention containing 18 mg. of zinc and 2 mg. of potassium formed with a polygalacturonic acid having n=about 140. The test results are shown in the following Table 5:

Table 5

| Name | Area of wound in $cm^2$ before treatment | Time to Complete healing in weeks |
|---|---|---|
| 1. Mrs. E. Cs. | 2.2 | 3 |
| 2. Mr. S. Cs. | 2.5 | 5 |
| 3. Mr. J. N. | 4.1 | 3 |

Table 5-continued

| Name | Area of wound in cm² before treatment | Time to Complete healing in weeks |
| --- | --- | --- |
| 4. Mr. S. F. | 6.2 | 8 |
| 5. Mr. P. N. | 5.7 | 6 |
| 6. Mrs. F. K. | 0.7 | 2½ |
| 7. Mr. J. K. | 0.4 | 2½ |
| 8. Mr. L. G. | 2.0 | 7 |
| 9. Mrs. L. K. | 4.0 | 4 |
| 10. Mrs. R. P. | 6.0 | 7 |
| 11. Mrs. J. K. | 4.0 | 7 |

Remark: note that the first seven subjects were treated with the complex of the invention, while the 8 to 11th subjects were treated with zinc sulfate Conclusion: the test data unambiguously prove that in the form of a complex of the invention a much smaller dose of zinc enables a complete healing within a shorter time than the zinc administered in the form of its sulfate.

(G) Using the complexes of the invention in geriatrics

It is known that the absorption of magnesium [J. Durlach: Symp. Int. Deficit. Magnesique Pathol. Hum., (C.R. 1st), 1971, Vittel (France)] and trace metals such as iron [A. Jacobs. and G. M. Owen: "Effect of age on iron absorption", J. Gerontol., 24, 95–96 (1969)], zinc and copper [M. Anke and H. J. Schneider: "Zinc, cadmium and copper metabolism in men", Arch. Exp. Veterinaermed., 25, 805–9 (1971)] and chromium [H. A. Schroeder: "Trace elements and Nutrition", Faber and Faber, London, 1973] significantly decreases and their secretion increases with the age. Due to these facts disorders such as anaemia, athero- and arteriosclerosis, diabetes mellitus, cardiovascular diseases (e.g. myocardial infarct), nephrolithiasis and ulcus emerge (see e.g. E. J. Underwood: "Trace elements in human and animal nutrition", Academic Press, N.Y. 1977). Therefore numerous vitamins and preparations containing essential elements are sold as geriatric preparations [see e.g. M. Heinitz: "Therapy with Minerals and Trace Elements in Geriatrics", Acta Gerontologie, 2, 175–9 (1972) and J. Bjorkstein: "A theoretical base for multivitamin therapy and for the first law of Le Compte", Rejuvenation, 4, 63–6 (1976)]. Accordingly, a preparation which makes possible the simple and efficient administering of the above trace elements is obviously desired.

elements is obviously desired.

In view of the fact that item A) to F) above prove that the complexes of the invention can be used for treating disorders which are characteristic in advanced age, these complexes should be considered as useful in geriatrics.

The invention is elucidated in detail by the aid of the following non-limiting Examples. In the Examples the preparation methods of oligo- and polygalacturonic acids used as starting substances are also given. The corresponding Examples (Examples 1 and 2) describe chemical hydrolysis methods, but enzymatic hydrolysis can also be performed.

EXAMPLE 1 Preparation of polygalacturonic acid from apple pectin 50 g. of apple pectin powder are homogenized with 1000 ml. of water in a mortar. The suspension is allowed to stand overnight, thereafter 4000 ml. of distilled water are added. The resulting homogeneous sol is rendered alkaline (pH-12) with a 0.1 n alkali hydroxide solution, thereafter 5 g. of sodium chloride or aluminium chloride are added to the mixture to catalyze the decomposition. The mixture is allowed to stand at room temperature (23° C.) for 2 hours; during this period the consumed alkali is continuously supplemented. After 2 hours of standing the mixture is acidified to pH=0.5 with concentrated hydrochloric acid, and the resulting partially esterified polygalacturonic acid is precipitated with alcohol. The obtained product is homogenized with distilled water, the pH of the mixture is adjusted to 4.5±0.5 with 0.1 n aqueous sodium hydroxide solution, and the mixture is allowed to stand overnight. The above hydrolysis and precipitation steps are repeated four times. The molecular weight polygalacturonic acid obtained as product is separated by centrifuging, washed with water, alcohol and ether, and dried at 60° C. 18 to 20 g. of polygalacturonic acid are obtained. The polymerization grade of the obtained product is about 140.

Analytical data: C: 40.1%; H: 4.9%; O: 55%; —OCH$_3$: 0.1%; —COOH: 5.6 meq./g., ash: 0.1%.

EXAMPLE 2

Preparation of decagalacturonic acid from polygalacturonic acid 25 g. of polygalacturonic acid, prepared as described in Example 1, are admixed with 800 to 900 ml. of 0.1 n aqueous sodium hydroxide solution, and the system with a pH value of 4.5 is allowed to stand overnight in order to achieve complete dissolution. The obtained homogeneous sol is acidified to pH 3 with about 150 ml. of 0.1 n aqueous sulfuric acid, and the mixture is boiled for one hour. The solution is cooled, the product is precipitated with alcohol, and the precipitated, purified substance is dried at 60° C. 18 to 20 g. of a product, consisting mainly of decagalacturonic acid and containing maximum 1% of higher or lower polymers, are obtained. The product decomposes at about 150° C.; it dissolves readily in aqueous acids (pH: 0 to 3).

Characteristic bands of the IR absorption spectrum: 3440 (—OH with H-bond), 2936 (aliphatic C-H), 2600 (dimeric —COOH), 1745 (aliphatic —COOH), 1400 (C-H deformation), 1330 (C-O-H deformation), 1216 (COH, OCH, CCH deformation), 1140 (CO, C-C, C-H), 1096, 1070, 1050 (COH deformation), 1020, 950, 880, 830 (pyrane ring, skeletal vibration), 630 (—OH deformation) cm$^{-1}$.

Analysis: Calculated for $C_{60}H_{82}O_{61}$: C: 40.5%, H: 4.6%, O: 54.9%; found: C: 40.1%, H: 4.1%, O: 55.8%.

EXAMPLE 3

Preparation of copper(II)-potassium-decagalacturonate 1 l. of a 0.1 molar copper(II) sulfate solution in distilled water is added to 10 l. of a 0.25% decagalacturonic acid solution in distilled water (original pH=3.0), the pH of which is adjusted to 5.3 by 2 n potassium hydroxide solution under vigorous stirring. A greenish-blue gel separates. The reaction mixture is allowed to stand overnight, thereafter the liberated sulfuric acid is neutralized with aqueous potassium hydroxide solution. The mixture is allowed to stand at room temperature for further 3 days, thereafter the supernatant is decanted and the gel-like residue is centrifuged. The obtained substance is suspended in about 2 l. of distilled water and centrifuged again. This washing operation is repeated 3 or 4 times in order to remove the traces of copper(II) sulfate. 391 g. of a gel, containing 4.7% by weight of dry substance are obtained. The gel is dried at 60° C. to obtain 22.3 g. of copper(II)-potassium-decagalacturonate.

Analysis: calculated for $[Cu(C_6H_7O_6)_2]_{10}(OH_2)_2$: Cu: 15.2%, C: 34.5%, H* 3.5%, O: 46.8%; calculated for $[K(C_6H_7O_6)]_{10}(OH_2)_2$: K: 18.1%, C: 33.4%, H: 3.4%, O: 45.2%; found: Cu: 13.5%, C: 32.9%, H: 3.8%, O: 49.3%, K: 0.5%.

EXAMPLE 4

Preparation of cobalt(II)-potassium-decagalacturonate 2. 1. of a 0.1 molar cobalt(II) sulfate solution are added, under vigorous stirring, to 8 1. of a 0.3% decagalacturonic acid solution in distilled water (original pH=3), the pH of which is adjusted to 6.0 by 2 n potassium hydroxide solution. A pink gel separates. The reaction mixture is allowed to stand overnight, and the liberated sulfuric acid is neutralized with aqueous potassium hydroxide solution. After 3 days of standing the gel is separated by centrifuging and washed with water in order to remove the traces of cobalt(II) sulfate. 1700 g. of a gel with a dry substance content of 1.5% by weight are obtained. The gel is dried at 60° C. to obtain 25.5 g. of cobalt(II)-potassium-decagalacturonate.

Analysis: calculated for $[Co(C_6H_7O_6)_2]_{10}(OH_2)_2$: Co: 14.3%, C: 34.9%, H: 3.5%, O: 47.3%; found: Co: 13.5%, C: 31.4%, H: 4.3%, O: 49.2%, K: 1.6.

EXAMPLE 5

Preparation of iron(II)-potassium-decagalacturonate 2 1. of a 0.1 molar aqueous iron(II) sulfate solution are added, under vigorous stirring, to 8 1. of a 0.3% aqueous decagalacturonic acid solution (original pH=3), the pH of which is adjusted to 5.0 by 2 n potassium hydroxide solution. In order to reduce the iron(III) irons optionally present, 2 g. of L-ascorbic acid or a small amount of iron powder is added to the iron(II) sulfate solution prior to introducing it into the mixture. A greenish-white gel separates. The liberated sulfuric acid is neutralized with aqueous potassium hydroxide solution, and the obtained mixture is allowed to stand at room temperature for 3 days. The gel is separated by centrifuging, and washed with dilute aqueous L-ascorbic acid solution in order to remove the traces of iron(II) sulfate. 579 g. of a gel with a dry substance content of 3.9% by weight are obtained. The gel is dried at 60° C. to obtain 22.6 g. of iron(II)-potassium-decagalacturonate.

Analysis: calculated for $[Fe(C_6H_7O_6)_2]_{10}(OH_2)_2$: Fe: 13.6%, C: 35.2%, H: 3.5%, O: 47.6%; found: Fe: 10.5%, C: 32.8%, H: 3.8%, O: 51.6%; K: 1.3.

EXAMPLE 6

Preparation of iron(II)-copper(II)-cobalt(II)-potassium-decagalaoturonate coprecipitate A homogeneous mixture of 1 1. of 0.1 molar aqueous iron(II) sulfate solution, 100 ml. of 0.1 molar aqueous copper(II) sulfate solution and 30 ml. of 0.1 molar aqueous cobalt(II) sulfate solution is added to 10 1. of a 0.3% aqueous decagalacturonic acid solution (pH=3) under vigorous stirring. In order to reduce the iron(III) ions optionally present, L-ascorbic acid is added to the sulfate solution prior to introducing it into the mixture. After one minute a mixture of 1 1. of 0.1 molar aqueous iron(II) sulfate solution (previously reduced with L-ascorbic acid) and 100 ml. of a 0.1 molar aqueous copper(II) sulfate solution is added to the system. A dark grayish-green precipitate separates. The liberated sulfuric acid is neutralized with aqueous potassium hydroxide solution. The gel is separated by centrifuging, washed with water until free of salts, and dried at 60° C. 30 g. of the desired coprecipitate are obtained.

Analysis: Fe: 4.8%, Cu: 4.35%, Co: 0.06%, K: 4.1% C: 39.0%, H: 5.95%, O: 46.5%.

The composition of the product can be modified by altering the ratios of the precipitants.

EXAMPLE 7

Preparation of zinc(II)-potassium-decagalacturonate 2 l. of a 0.1 molar zinc(II) sulfate solution are added to 8 1. of a 0.3% aqueous decagalacturonic acid solution (original pH=3), the pH of which is adjusted to 6.0 by 2 n potassium hydroxide solution, under vigorous stirring. A white, fluffy gel separates. The liberated sulfuric acid is neutralized with aqueous potassium hydroxide solution, and the mixture is allowed to stand at room temperature for 3 days. Thereafter the gel is separated by centrifuging and washed with water in order to remove the traces of zinc(II) sulfate. 700 g. of a gel with a dry substance content of 2.6% by weight are obtained. The gel is dried at 60° C. to obtain 18.2 g. of zinc(II)-potassium-decagalacturonate.

Analysis: calculated for $[Zn(C_6H_7O_6)_2]_{10}(OH_2)_2$: Zn: 15.6%, C: 34.4%, H: 3.5%, O: 46.6%; found: Zn: 12.2%, C: 33.3%, H: 4.2%, O: 51.0%; K: 1.3%.

EXAMPLE 8

Preparation of manganese(II)-potassium-decagalacturonate 2 1. of a 0.1 molar manganese(II)-acetate solution are added, under vigorous stirring, to 7 1. of a 0.3% aqueous decagalacturonic acid solution (original pH=3), the pH of which is adjusted to 8.0 by 2 n potassium hydroxide solution. A brown gel separates. The liberated acetic acid is neutralized with aqueous potassium hydroxide solution, and the mixture is allowed to stand at room temperature for 3 days. The gel is separated by centrifuging and washed with water in order to remove the traces of manganese(II)-acetate. 1105 g. of a gel with a dry substance content of 2.2% by weight are obtained. The gel is dried at 60° C. to obtain 24.3 g. of manganese(II)-potassium-decagalacturonate.

Analysis: calculated for $[Mn(C_6H_7O_6)_2]_{10}(OH_2)_2$: Mn: 13.4%, C: 35.3%, H: 3.6%, O: 47.8%; found: Mn: 10.9%, C: 34.6%, H: 4.5%, O: 47.0%; K: 3.0%

EXAMPLE 9

Preparation of magnesium(II)-potassium(I)-decagalacturonate coprecipitate 400 ml. of a 1 molar aqueous magnesium sulfate solution are added, under vigorous stirring, to 7 1. of a 0.3% aqueous decagalacturonic acid solution (pH=3). A white gel separates. The mixture is allowed to stand at room temperature for one day, thereafter it is rendered alkaline with aqueous potassium hydroxide solution, and maintained at room temperature for further 3 days. The gel is separated by centrifuging and washed thrice with 10% aqueous ethanol. 870 g. of a gel with a dry substance content of 2.5% by weight are obtained. The gel is dried at 60° C. to obtain 21.7 g. of magnesium(II)-potassium(I)-decagalacturonate coprecipitate.

Analysis: calculated for $[Mg(C_6H_7O_6)_2]_{10}(OH_2)_2$: Mg: 6.4%, C: 38.1%, H: 3.8%, O: 51.6%. Found: Mg: 5.5%, K: 2.8%, C: 34.9%, H: 4.7%, O: 49.9%.

EXAMPLE 10

Preparation of nickel(II)-potassium-decagalacturonate 1 l. of a 0.2 molar aqueous nickel(II) chloride solution is added to 6 l. of a 0.3% aqueous decagalacturonic acid solution (original pH=3), the pH of which is adjusted to 6.5 by 2 n potassium hydroxide solution, under slow stirring. A light greenish-brown gel separates. The mixture is allowed to stand at room temperature for one day, and the liberated hydrochloric acid is neutralized with aqueous potassium hydroxide solution. The mixture is allowed to stand at room temperature for one week. The separated gel is removed by centrifuging and washed in order to remove the traces of nickel(II) chloride. 700 g. of a gel with a dry substance content of 2.6% by weight are obtained. The gel is dried at 60° C. to obtain 17.5 g. of nickel(II)-potassium-decagalacturonate.

Analysis: calculated for $[Ni(C_6H_7O_6)_2]_{10}(OH_2)_2$: Ni: 14.2%, C: 34.9%, H: 3.5%, O: 47.3%; found: Ni: 11.0%, C: 30.3%, H: 4.3%, O: 49.0%, K: 3.4%

EXAMPLE 11

Preparation of chromium(III)-potassium-decagalacturonate 1 l. of a 0.06 molar chromium(III) sulfate solution is added to 7 l. of a 0.3% aqueous decagalacturonic acid solutoin (original pH=3), the pH of which is adjusted to pH=4.5 by 2 n potassium hydroxide solution, with stirring. A violet gel separates. The mixture is allowed to stand overnight, then the liberated sulfuric acid is neutralized with sodium hydroxide solution. 1860 g. of a gel with a dry substance content of 1%, corresponding to the empirical formula $[Cr(H_2O)_6(C_6H_7O_6)_3]_{10}(OH_2)_3$ are obtaned. When heated at 80° C., the gel loses water and converts into a greenish substance corresponding to the empirical formula $[Cr(C_6H_7O_6)_3]_{10}(OH_2)_3$.

Analysis: calculated for $[Cr(C_6H_7O_6)_3]_{10}(OH_2)_3$: Cr: 8.9%, C: 37.1%, H: 3.7%, O: 50.2%; found: Cr: 8.0%, C: 30.2%, H: 3.9%, O: 54.2%, K: 3.7%.

The gel obtained by the above process is an outersphere aquocomplex. The inner-sphere complex can be prepared as follows:

1 l. of a 0.033 molar aqueous potassium bichromate solution, acidified with dilute sulfuric acid to pH=3, is added to 10 l. of a 0.25% aqueous decagalacturonic acid solution (pH=3). The resulting mixture is stirred vigorously for 5 minutes, thereafter heated to 60° C., and 100 ml. of a 1 molar aqueous hydrazine sulfate solution, pre-heated to 60° C., are added to the mixture under vigorous stirring. The mixture turns first to orange, then to yellowish brown, later on to brownish green, and finally a green gel separates under nitrogen evolution. The mixture is allowed to stand overnight, then the liberated sulfuric acid is neutralized with aqueous potassium hydroxide solution. The resulting mixture is allowed to stand for 3 days. The gel is separated by centrifuging and washed four times with water in order to remove the traces of hydrazine sulfate. The gel is dried at 105° C. to obtain 23 g. of chromium(III)-potassium-decagalacturonate.

Analysis: calculated for $[Cr(C_6H_7O_6)_3]_{10}(OH_2)_3$: Cr: 8.9%, C: 37.1%, H: 3.7%, O: 50.2%; found: Cr: 8.9%, C: 29.5%, H: 3.9%, O: 56.9%, K: 0.8%.

EXAMPLE 12

Preparation of molybdenyl-potassium-decagalacturonate 7 l. of a 0.3% aqueous decagalacturonic acid solution (pH=3) are heated to boiling, and 200 ml. of a hot 1 molar aqueous solution of potassium molybdate (pH=7) and 1 g. KCl are added to the hot solution. The resulting hot, homogeneous mixture (pH=5) is stirred vigorously, and a large excess (200 ml.) of a 1 molar aqueous hydrazine dichloride solution is added. A dark blue solution forms, from which a dark blue precipitate separates. The precipitate is separated by centrifuging, washed once with water, and dried at 60° C. 30 g. of molybdenyl-potassium-decagalacturonate are obtained.

Based on ESR examination, the product contains molybdenum in pentavalent state as molybdenyl(I) ions. Thus the emprical formula of the product is $[\{Mo(O)K_3\}(C_6H_7O_6)_3]_{10}(OH_2)_3$.

Analysis: calculated for $[Mo(O)(C_6H_7O_6)_3]_{10}(OH_2)_3$ Mo: 15.9%, C: 33.6%, H: 3.4%, O: 45.8%; found: Mo: 17.5%, C: 31.5%, H: 3.1%, O: 46.8%, K: 1.1%.

Vanadyl decagalacturonate can be prepared by a similar reaction.

EXAMPLE 13

Preparation of chromium(III)-manganese(II)-zinc(II)-copper(II)-magnesium(II)-potassium(I)-decagalacturonate coprecipitate A homogeneous mixture of 1 l. of a 0.1 molar aqueous manganese(II)-sulfate solution, 300 ml. of a 0.1 molar aqueous zinc(II) sulfate solution, 60 ml. of a 0.1 molar aqueous copper(II) sulfate solution, 10 ml. of a 0.06 molar aqueous chromium(III) sulfate solution, 100 ml. of a 1 molar aqueous magnesium sulfate solution and 10 ml. of a 1 molar aqueous potassium chloride solution is added to 10 l. of a 0.3% aqueous decagalacturonic acid solution (pH=3) under vigorous stirring. After 1 minute of stirring the pH of the mixture is adjusted to 4.5 with 0.1 n aqueous potassium hydroxide solution. The mixture containing a greenish-brown precipitate is allowed to stand for 3 days, thereafter the gel is separated by centrifuging, washed and dried at 60° C. 25 g. of a coprecipitate are obtained.

Analysis: Mg: 3%, K: 1%, Cr: 0.09%, Mn: 2.6%, Zn: 2.2%, Cu: 0.7%.

EXAMPLE 14

Preparation of iron(II)-copper(II)-cobalt(II)-zinc(II)-manganese(II)-magnesium(II)-chromium(III)-potassium(I)-decagalacturonate coprecipitate A homogeneous mixture of 500 ml. of a 0.1 molar aqueous iron(II) sulfate solution, 50 ml. of a 0.1 molar aqueous copper(II) sulfate solution, 15 ml. of a 0.1 molar aqueous cobalt(II) sulfate solution, 500 ml. of a 0.1 molar aqueous manganese(II) sulfate solution, 150 ml. of a 0.1 molar aqueous zinc(II) sulfate solution, 5 ml. of a 0.06 molar aqueous chromium(III) sulfate solution, 50 ml. of a 1 molar aqueous magnesium sulfate solution and 10 ml. of a 1 molar aqueous potassium chloride solution is added to 10 l. of a 0.3% aqueous decagalacturonic acid solution under stirring, and the pH of the mixture is adjusted to 4.5 with aqueous potassium hydroxide solution. The separated black precipitate is removed by centrifuging, washed, and dried at 60° C. 26 g. of the desired coprecipitate are obtained.

Analysis: Mg: 1%, K: 0.1%, Cr: 0.05%, Mn: 1%, Zn: 1.3%, Cu: 0.8%, Fe: 2%, Co: 0.03%.

EXAMPLE 15

Preparation of iron(II)-potassium(I)-polygalacturonate 250 g. of polygalacturonic acid, prepared as described in Example 1, are suspended in 20 l. of distilled water, and the pH of the suspension is adjusted to 5.5 with about 600 to 700 ml. of a 2 n aqueous potassium hydroxide solution. The mixture is allowed to stand overnight in order to achieve dissolution. The resulting homogeneous sol is admixed under vigorous stirring with 10 l. of a 0.1 molar aqueous iron(II) sulfate solution. A greenish-white gel separates. The liberated sulfuric acid is neutralized with aqueous potassium hydroxide solution, and the obtained mixture is allowed to stand at room temperature for 3 days. The gel is separated by centrifuging and washed thrice with distilled water in order to remove the traces of iron(II) sulfate. The gel is dried at 60° C. 275 g. of iron(II)-potassium(I)-polygalacturonate are obtained.

Analysis: Fe: 7.7%, C: 31.0%, H: 3.9%, K: 6.9%, O: 50.4%.

EXAMPLE 16

Preparation of copper(II)-potassium(I)-polygalacturonate 250 g. of polygalacturonic acid, prepared as described in Example 1, are suspended in 20 l. of distilled water, and the pH of the suspension is adjusted to 5 with about 500 ml. of a 2 n aqueous potassium hydroxide solution. The mixture is allowed to stand overnight in order to achieve dissolution. 10 l. of a 0.1 molar aqueous copper(II) sulfate solution are added to the resulting homogeneous sol, upon which a green gel separates. The gel is separated by centrifuging and washed thrice with distilled water in order to remove the traces of copper(II) sulfate. The gel is dried at 60° C. to obtain 286 g. of copper(II)-potassium(I)-polygalacturonate.

Analysis: Cu: 11.4%, K: 3.9%, C: 32.9%, H: 5.0%, O: 47%.

EXAMPLE 17

Preparation of cobalt(II)-potassium(I)-polygalacturonate 250 g. of polygalacturonic acid, prepared as described in Example 1, are suspended in 20 l. of distilled water, and the pH of the suspension is adjusted to 6.5 with about 800 ml. of a 2 n aqueous potassium hydroxide solution. The mixture is allowed to stand overnight in order to achieve dissolution. 10 l. of a 0.1 molar aqueous cobalt(II) sulfate solution are added to the resulting homogeneous sol under vigorous stirring. A pink gel separates. The liberated sulfuric acid is neutralized with aqueous potassium hydroxide solution, and the resulting mixture is allowed to stand at room temperature for 3 days. The gel is separated by centrifuging and washed thrice with distilled water in order to remove the traces of cobalt(II) sulfate. The gel is dried at 60° C. to obtain 280 g. of cobalt(II)-potassium(I)-polygalacturonate.

Analysis: Co: 9.0%, K: 5.5%, C: 31.6%, H: 5.6%, O: 48%.

EXAMPLE 18

Preparation of iron(II)-copper(II)-cobalt(II)-potassium(I)-polygalacturonate coprecipitate 250 g. of polygalacturonic acid, prepared as described in Example 1, are suspended in 20 l. of distilled water, and the pH of the suspension is adjusted to 4.5 with about 500 ml. of a 2 n aqueous potassium hydroxide solution. The mixture is allowed to stand overnight in order to achieve dissolution. 10 l. of an aqueous metal salt solution, 0.1 molar for iron(II) sulfate, 0.01 molar for copper(II) sulfate and 0.001 molar for cobalt(II) sulfate, are added to the resulting honogeneous sol under vigorous stirring. A dark greenish-grey gel separates. The liberated sulfuric acid is neutralized with aqueous potassium hydroxide solution, and the resulting mixture is allowed to stand at room temperature for 3 days. The gel is separated by centrifuging, washed thrice with distilled water, and dried at 60° C. to obtain 247 g. of the desired coprecipitate.

Analysis: Fe: 5.2%, Cu: 4.1%, Co: 0.05%, C: 39.1%, H: 5.9%, O: 45%, K: 4.3%.

EXAMPLE 19

Preparation of tablets

A mixture of 400 mg. of magnesium-potassium-decagalacturonate, prepared as described in Example 9, and 100 mg. of iron(II)-copper(II)-cobalt(II)-decagalacturonate, prepared as described in Example 6, is ground to a fine powder, and the powder is compressed into tablets weighing 0.5 g. each. For the treatment of anaemia 1 to 3 tablets are administered daily to the patient.

EXAMPLE 20

Preparation of tablets 1000 mg. of finely ground decagalacturonic acid, 695 mg. of finely ground iron(II) sulfate heptahydrate, 62.42 mg. of finely ground copper(I) sulfate pentahydrate and 7.025 mg. of cobalt(II) sulfate heptahydrate are thoroughly blended. 235.5 mg. of pectin are added to the mixture as binding agent. The mixture is homogenized again, and then compressed into tablets, weighing 0.5 g. each, under very high pressure (10 tons/cm$^2$). Upon the effect of the high pressure a reaction sets in, and the metal complexes of decagalacturonic acid form in solid phase.

What we claim is:

1. A method for treating a deficiency of at least one of the element selected from the group consisting of iron-(II), copper(I), copper(II), magnesium(II), cobalt(II), manganese(II), zinc(II), chromium(III), molybdenum(V), vanadium(IV) and nickel(II), in humans, comprising administering to a human suffering from said deficiency an effective amount per day of said at least one of said elements plus potassium in the form of their complex formed with an oligo- or plygalacturonic acid of the formula

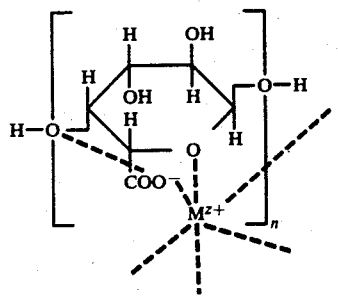
wherein
n is an integer from 10 to 145,
M is said at least one metal cation selected from said group plus potassium, and
Z is an integer corresponding to the charge or the valence number of the metal atom, said amount being effective to relieve said deficiency.
* * * * *